United States Patent [19]

Pry et al.

[11] Patent Number: 5,229,268

[45] Date of Patent: * Jul. 20, 1993

[54] METHOD FOR DIAGNOSTIC IMMUNOASSAY BY SOLID PHASE SEPARATION

[75] Inventors: Terry A. Pry, Libertyville; Edward N. Granados, Vernon Hills; Philip M. Hill, Waukegan, all of Ill.

[73] Assignee: Abbott Laboratories, Abbott Park, Ill.

[*] Notice: The portion of the term of this patent subsequent to Nov. 29, 2008 has been disclaimed.

[21] Appl. No.: 172,503

[22] Filed: Nov. 24, 1987

Related U.S. Application Data

[63] Continuation-in-part of Ser. No. 885,130, Jul. 14, 1986, abandoned.

[51] Int. Cl.⁵ ............... G01N 33/563; G01N 33/552; G01N 33/537
[52] U.S. Cl. .................... 435/7.92; 436/518; 436/523; 436/528; 436/538; 436/539; 436/541; 436/177; 436/824; 530/413
[58] Field of Search ............ 435/7, 7.9, 7.92; 436/518, 523, 528-534, 538, 539, 541, 177, 824, 815-818; 530/413

[56] References Cited

U.S. PATENT DOCUMENTS

| | | | |
|---|---|---|---|
| 4,115,537 | 9/1978 | Driscoll et al. | 436/541 X |
| 4,135,880 | 1/1979 | Mangiardi et al. | 436/541 X |
| 4,166,104 | 8/1979 | Wagner et al. | 436/539 X |
| 4,170,454 | 10/1979 | Meriadec et al. | 436/535 |
| 4,200,436 | 4/1980 | Mochida et al. | 436/531 X |
| 4,211,763 | 7/1980 | Marshall et al. | 436/541 X |
| 4,224,439 | 9/1980 | Ayers et al. | 536/32 |
| 4,330,440 | 5/1982 | Ayers et al. | 525/54.31 |
| 4,551,426 | 11/1985 | Freytag et al. | 435/7 |
| 4,656,143 | 4/1987 | Baker et al. | 436/538 X |
| 4,788,136 | 11/1988 | Grenier et al. | 435/7 |

OTHER PUBLICATIONS

"Modern Granulation, Tabletting and Capsule Technology" published by the Institute for Applied Pharmaceutical Science (1985) pp. 48-57.
Miron, et al., *Applied Biochemistry and Biotechnology*, 11:445-456 (1985).
Shih, et al., *Biochemistry*, 13:3411-3418 (1974).
Saxinger, et al., *PNAS*, 69:2975-2978 (1972).

*Primary Examiner*—Esther L. Kepplinger
*Assistant Examiner*—Carol A. Spiegel
*Attorney, Agent, or Firm*—Lawrence S. Pope; Thomas M. Breininger; Daniel W. Collins

[57] ABSTRACT

A method for performing a diagnostic immunoassay by a solid phase separation. To a reaction mixture of a test sample and labeled antibody, which forms a complex of any analyte present in the test sample, is added a solid phase material having a compound capable of binding any excess labeled antibody. The solid phase material is chosen to rapidly settle whereby a solid and liquid phase is formed. The liquid phase can then be extracted to measure the amount of analyte-labeled antibody present therein.

19 Claims, 1 Drawing Sheet

METHOD FOR DIAGNOSTIC IMMUNOASSAY BY SOLID PHASE SEPARATION

BACKGROUND OF THE INVENTION

This application is a continuation-in-part of application Ser. No. 885,130 filed July 14, 1986, entitled "Method for Diagnostic Immunoassay by Solid Phase Separation", now abandoned.

The present invention is directed toward a method for performing a diagnostic immunoassay for the measurement of small and large proteins and analytes in biological fluids by a solid phase separation. This method is especially suitable for use in automated systems.

Many diagnostic immunoassays are known which generally employ the specific binding characteristics that exist between an analyte or protein with a specific antibody tagged with some traceable substituent. One problem which has long been associated with this method is how to remove excess antibody from the biological fluid being tested for concentration of analyte in a manner whereby the analyte concentrations can be accurately measured.

Various attempts to remove excess antibody include U.S. Pat. No. 4,298,682 which discloses the absorption of unreacted antibody on a solid phase consisting of a polyacrylamide gel sensitized to the specific antibody.

U.S. Pat. No. 4,551,426 discloses another method to remove excess antibody in an immunoassay for digoxin. Here, excess labeled antibody is removed by passing it through an affinity column that has ouabain, an analog of digoxin, immobilized on the solid phase chromatography matrix. The excess antibody is absorbed by the ouabain. The chromatography elute is then examined for the labeled antibody analyte complex.

While the above can be effective, they are all subject to improvement, especially with respect to ease in operation, handling and thereby accuracy. The subject method provides improvements over these methods and is especially adaptable to automated analysis which is not the case with many of the known methods.

SUMMARY OF THE INVENTION

The present invention is directed toward a method for conducting a diagnostic immunoassay. The steps of the method comprise (a) forming a reaction mixture of a test sample with a molar excess of labeled antibody to form a complex of analyte present in the test sample, (b) contacting the reaction mixture with a solid phase material having immobilized thereon a compound in an amount sufficient to complex with any of the excess labeled antibody employed in step (a), (c) allowing the solid phase material and any complex of the solid phase material to settle and form a solid and liquid phase, and (d) measuring the amount of complex present in the liquid phase.

Generally, the solid phase material is of sufficient density to rapidly sediment by gravity. Preferably the solid phase material has a sedimentation rate of about 5 seconds to about 2 minutes per centimeter in water and is from about 5 to about 300 microns in diameter. The solid phase material can be formed of any of a variety of materials, preferably, agarose, polystyrene, polyacrylamide, their derivatives or mixtures thereof.

The solid phase material has immobilized thereon a compound capable of binding the excess labeled antibody such as a corresponding antigen or chemical analogue. Typically, the labeled antibody is an enzyme labeled antibody.

The present invention also involves adding an aliquot of the solution from which excess antibody must be removed to a tabletted reagent. The tabletted reagent includes from about 10 to 80 percent microcrystalline cellulose, and from about 20 to 90 percent of water insoluble polymeric particles to which a ligand specific to the antibody is bound or to which an anti-ligand antibody is bound in the event that ligand is to be removed from solution. When the solution is added to the tablet, the microcrystalline cellulose and the polymeric particles absorb water but remain in particulate form such that the tablet readily disintegrates. Both the cellulose and polymeric particles settle to the bottom of the solution. As the polymeric particles settle, the ligand bound to the polymeric particles attract excess antibody so that the excess antibody settles with the polymeric particles to the bottom of the solution. The result, the tabletted reagent of the present invention removes the antibody without leaving any material in the sample which interferes with the analysis being performed. Everything in the tablet settles to the bottom of the solution. The solution can simply be decanted to remove the unwanted antibody. With the tabletted reagent, a precise, known quantity of ligand coated particles can be added to the solution. The possibility of an insufficient amount of ligand-coated particles being added to the solution is minimized as compared with the slurry technique.

The present method is particularly adapted for use in automated diagnostic apparatus where centrifugation filtration or column filtration is not possible or practical.

DETAILED DESCRIPTION OF THE INVENTION

Figure 1:
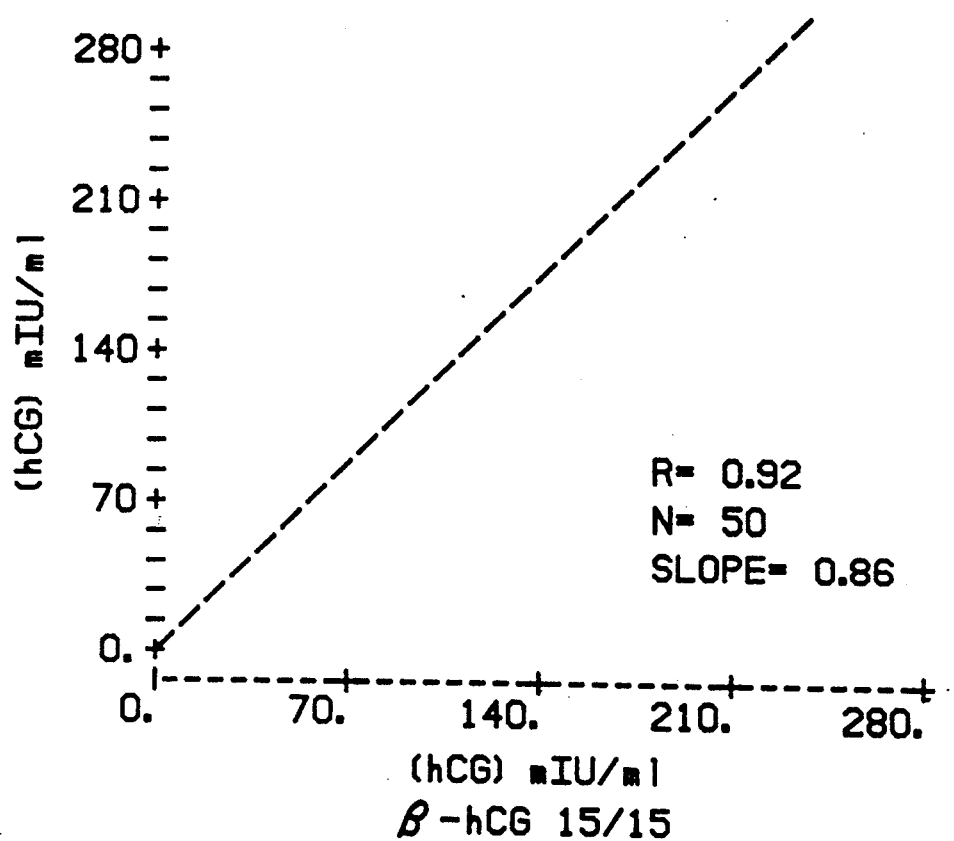
FIG. 1 is a graph of the correlation of the data obtained with the subject method versus a standard method (Abbott $\beta$-hCG 15/15).

The present invention provides for a method whereby any excess labeled compound employed to identify a particular analyte can be readily removed to permit measurement of the analyte. The method, as outlined below, is particularly adapted for use in automated systems where traditional purification or removal means are not appropriate, i.e., filtration, centrifugation or filtration columns. More preferably the subject method is employed with the diagnostic immunoassay apparatus TDx ™, a trademark of Abbott Laboratories for an automated system for the quantitation of therapeutic drug concentrations in serum or plasma based on the method of fluorescence polarization immunoassay.

Generally, the method comprises the preparation of a reaction mixture of a biological fluid suspected of containing a known analyte, or protein with a labeled substance, antibody, capable of complexing with the particular analyte, protein or material sought to be quantified. The labeled substance is added to the reaction mixture in a molar excess with regard to the suspected amount of material to be quantified to assure complete complexing thereof.

After an appropriate incubation time, i.e., sufficient time to allow the labeling substance to complex with all the material sought to be quantified, the complex is measured. However, because the labeling substance is employed in a molar excess it is necessary to remove this excess prior to measuring the amount of complex formed.

The subject method is characterized by removing the excess labeled substance by adding a solid phase material having immobilized thereon a compound capable of complexing with the labeled substance. The solid phase material is of such physical characteristics that it can be easily dispersed in the reaction mixture and settled out. Therefore the density and overall size of the solid phase material is such that a rapid disperse by agitation and sediment by gravity is facilitated.

The solid phase material is present as a particle or matrix having a density greater than water. The solid phase material has a sedimentation rate in water of from about 5 seconds per centimeter to about 2 minutes per centimeter, more preferably from about 20 seconds per centimeter to about 1.5 minutes per centimeter. The size of particle which forms the solid phase material can be from about 5 microns to about 300 microns, preferably from about 40 microns to about 120 microns in diameter. The sedimentation rate and size is important to assuring the solid phase material both disperses and settles readily without significant input of energy or motion to the reaction vessel containing the subject reaction mixture. This is especially important when employing automated diagnostic apparatus.

The solid phase material can be fabricated from any number of material or synthetic materials. Preferably the solid phase material is manufactured from polymeric materials such as agarose, polystyrene, polyacrylamide, their derivatives or mixtures thereof. Generally the solid phase is present as bead-like structures. The solid phase material can be delivered to the reaction vessel as a dry powder, wet slurry, tablet or a capsule.

Immobilized on the solid phase material is a compound capable of complexing the labeled substance. Generally this is a complimentary substance to the substance to be identified. Examples include an analyte, or its analog. The complex formed is bonded to the solid phase material and because of its physical characteristics settles out or sediments by gravity. The total reaction mixture thus becomes separated into a solid phase containing the solid phase material complexed with any excess labeled substance and a liquid phase containing the material sought to be quantified which is complexed to the labeled substance.

The liquid phase is then measured for amount of the material sought to be quantified, i.e., analyte or protein. Generally this is accomplished by extracting the liquid phase by syringe, suction, or other means. An appropriate immunoassay format is then employed to measure the amount of labeled substance consistent with the particular label employed.

Typical labeling means can include enzymes, radioisotopes, chromophores, fluorophores or any substance which is capable of generating a detectable signal, either alone or in combination with other reagents. Procedures and methods for labeling and identifying the labeled complexes are well known in the art of diagnostic immunoassay as is generally discussed in L. Miles and C. Hales, *Labeled Antibodies and Immunological Assay Systems*, Nature 219, 187–189 (1968) and U.S. Pat. No. 3,654,090.

The subject method is especially useful in an automated diagnostic immunoassay apparatus because of its relatively automatic purification of the complex to be measured. Particularly, the immunoassay method can be conducted by mixing the biological fluid to be analyzed with sufficient labeled substance and then adding this reaction mixture to a vessel containing the subject solid phase material or adding the subject solid phase material to the initial reaction mixture wherein the subject solid phase material purifies the reaction mixture of excess labeled substance without requiring additional physical or chemical treatment steps. Thus, the subject method avoids the necessity to centrifuge, prepare an elute from a column, or other more tedious steps to obtain the labeled substance for final measurement.

The tabletted reagent of the present invention includes about 10 to 80 percent microcrystalline cellulose, and about 20 to 90 percent of water insoluble polymeric particles to which a ligand or anti-ligand antibodies are bound. Preferably, the reagent includes about 40–60 percent of the cellulose, and 40–60 percent of the particles. A fifty fifty mixture has worked quite nicely.

The polymer used for the particles can include a cross-linked dextran, agarose, or a polyacrylamide. A polyacrylamide is the most preferred because it is hydrophilic and is easy to conjugate with ligands or anti-ligand antibodies, yet will settle quickly from solution.

Ligands which can be bound to the particles include, but are not limited to, a ouabain triacetate, tetrahydrocannabinal lysergic acid (LSD), cocaine (its metabolites or analogs), and the like. Anti-ligand antibodies which can be bound to the particles include anti-hCG antibody and the like.

The tabletted reagent of this invention is formed from two components, each of which has the consistency of a flour which can be pressed into tablets which are quite hard. However, the reagent can be tabletted easily (e.g. does not stick to or break upon ejection from tableting equipment and disintegrate completely when added to water.

Further details of this invention can be seen from the examples which follow which are illustrative and not intended to restrict the scope of this invention.

EXAMPLE 1

A method for measurement of both small or large analytes in a sample fluid. The assay format consisting of preincubation of excess enzyme-labeled antibody with sample such that sample is quantitatively and rapidly bound to form an analyte enzyme labeled antibody conjugate. An aliquot of this mixture is transferred to a vessel containing a solid phase material consisting of an analyte covalently coupled to a polymeric bead having a characteristic density to be easily suspended in solution yet sufficiently dense to rapidly sediment by gravity. The solid phase material rapidly captures the excess unconjugated enzyme-labeled antibody and sediments. Following the capture reaction and sedimentation an aliquot containing analyte-enzyme-labeled antibody is transferred to a cuvette for quantitation of enzyme using a fluorogenic substrate. The signal generated is proportional to the analyte concentration in the sample.

EXAMPLE 2 a) preparation of Enzyme Labeled Antibody

An enzyme labeled antibody of $\beta$-galactosidase conjugated to rabbit anti-digoxin F(ab')$_2$ was prepared. Rabbit antiserum against digoxin was fractionated by means of $(NH_4)_2SO_4$ and affinity chromatography on agarose-bovine serum albumin-ouabain. The resulting digoxin specific antibody was reacted with pepsin to produce F(ab')₂ (antibody fragments). This was coupled to *E. coli* β-galactosidase according to the procedure disclosed by Kitagawa and Aikawa, J. Biochem. 79:233 (1976). F(ab)₂-β-galactosidase was isolated by column chromatography.

b) Preparation of Solid Phase Material

Bovine serum albumin-digoxin was prepared as disclosed in PNAS 57:71 (1967). The product was dialyzed against a 0.1M Hepes buffer (7.5 pH) and concentrated to give a 5 mg/ml solution. An 8 ml aliquot of this solution was added to 15 ml of 300 micron agarose bead having an average diameter of 300 microns (purchased as Bio-Rad AFFI-GEL ® 15 from Bio-Rad Laboratories). The resulting agarose bovine serum albumin digoxin beads were washed with 4 molar quanidine hydrochloric acid and phosphate buffered saline.

Serum solutions containing 0, 1.0, 2.0, 3.0 and 5.0 nanograms per milliliter of digoxin were each tested following the same assay protocol as described below. A control was also run with zero digoxin and no solid phase material. To a 0.05 ml of serum sample was mixed 1 microliter of the enzyme labeled antibody as prepared (a), above. The reaction mixture was incubated at 34° C. for ten minutes and then a 20 microliter aliquot material (20:1 ratio) prepared from (b), above, with a 0.01 M phosphate buffer, pH 7.4 The mixture was incubated at 34° for 30 minutes with mixing.

The mixture was allowed to briefly rest whereupon it separated into a liquid and solid phase. The β-galactosidase activity of the supernatant was measured by quantitating the production of fluorescein. The measurement was conducted with a 10 micromolar solution of di-(β-D-galactosyl) fluorescein as a substrate and an assay buffer containing 0.1 M sodium phosphate, bovine gamma globulin, and 0.1% sodium azide at a pH of 7.4.

The measurements were as follows:

| Test No. | Digoxin Concentration (nanograms/ml) | Measured Fluorescence Rate |
|---|---|---|
| Control (no solid phase material) | 0.0 | 1370 |
| 1 | 0.0 | 95 |
| 2 | 1.0 | 110 |
| 3 | 2.0 | 125 |
| 4 | 3.0 | 170 |
| 5 | 5.0 | 245 |

The measurements obtained show that by employing the subject method a standard curve can be made to analyze serum solutions containing unknown digoxin concentrations. Also, the zero concentration measurement as compared to the control shows that the excess antibody conjugate was effectively removed by the subject method.

EXAMPLE 3 a) Preparation of F[ab']₂-Galactosidase Conjugates

Specific human chorionic gonadotropin (HCG) antibodies were immunopurified from rabbit antibodies (IgG), that were prepared by successive ammonium sulfate precipitations of anti-HCG rabbit sera, by using an HCG-immunoadsorbant. The HCG-immunoadsorbant was prepared by immobilizing HCG on AFFI-GEL ® 15 using conventional procedures that are described in the Bio-Rad literature available with AFFI-GEL ® 15.

For immunopurification the IgG was loaded on the HCG-AFFI-GEL ® 15 column that had been previously washed with 4.0 M Guanidine HCl, 1.0 M acetic acid and tris-buffered saline (TBS). The column was then washed extensively with TBS and eluted with 1.0 M acetic acid. The purified hCG specific antibodies obtained in the elute were extensively dialyzed against 0.1 M sodium acetate pH 4.5.

Fragments [F(ab')₂] of the hCG specific antibodies were prepared by digesting the said antibodies with pepsin and then isolating the F(ab')₂ fragments from the digestion mixture by column chromatography.

In order to prepare F(ab')₂-galactosidase conjugates the F(ab')₂ fragments were reacted with m-maleimidobenzoic acid N-hydroxysuccinimido ester (MBS). The resulting MBS derivitized fragments were purified by column chromatography and then subsequently reacted with *E. coli* β-galactosidase that had been previously purified by column chromatography. The F(ab')₂-galactosidase conjugates produced were isolated from unreacted galactosidase and unreacted F(ab')₂ by size exclusive chromatography.

b) Synthesis of hCG Solid Phase Reagent

The hCG-solid phase reagent was prepared by coupling hCG to TRISACRYL ® GF 2000LS.

TRISACRYL is a porous, spherical, polyacrylamide solid phase matrix available from the LKB Corporation, Gaithersburg, Md. Prior to coupling with hCG the TRISACRYL was activating by extensive washing with water, ethanol, acetone and dimethylformamide (DMF) and then reacting the TRISACRYL with carbonyl diimidizole (CDI) in DMF. The activated TRISACRYL was then coupled to hCG by the reaction of hCG with the said material in aqueous buffer (pH 10.2). Following the coupling unreacted hCG was removed from the TRISACRYL by extensive washing with 1.0 M acetic acid and neutral pH buffers.

c) Analysis of Serum hCG Levels

Serum solutions containing known amounts of hCG were used to generate a standard curve according to the following protocol: 25 ul of F(ab')₂ galactosidase, synthesized in (A) above, was added to 100 ul of sample and 50 ul TDx buffer. The reaction mixture was incubated at 34 degrees C for 2 minutes 20 seconds and then 50 ul of the reaction mixture, along with 60 ul of TDx buffer, was added to a slurry that consisted of 50 ul of hCG-TRISACRYL, synthesized in (B) above, and 10 ul of TDx buffer. This mixture was incubated at 34 degrees C. for 10 minutes with mixing. The mixture was allowed to briefly rest whereupon it separated into a liquid and solid phase. The galactosidase activity of the supernatant was measured by quantitating the production of fluorescein. The measurement was conducted with 10 micromolar solution of di(β-D-galactosyl) fluorescein as a substrate and an assay buffer containing 0.1 M sodium phosphate bovine gamma globulin, and 0.1% sodium azide at a pH of 7.4.

Table 1 shows the sensitivity obtained with various lots of hCG-TRISACRYL. The results indicate that the sensitivity obtained is not critically dependent on the amount of hCG coupled to the TRISACRYL in the 454–50 IU/ml range.

FIG. 1 shows the results for fifty clinical samples (N=50) that were measured for hCG content using a reference method (Abbott 8-hCG 15/15) and the subject method. A correlation coefficient of R=0.92 and a slope of 0.86 were obtained from analysis of the data shown in FIG. 1. These results indicate that the subject method is accurately measuring serum levels of hCG.

TABLE 1

Comparison of Sensitivity of Various Lots of hCG TRISACRYL

| Lot No. | hCG Coupled to TRISACRYL (IU/ml) | Sensitivity (mIU/ml) |
|---------|----------------------------------|----------------------|
| A | 454 | 10.0 |
| B | 151 | 10.0 |
| C | 50 | 12.5 |
| D | 17 | 25.0 |

EXAMPLE 4

Preparation of Ligand Labeled Tableted Reagent

A) Ligand-coupled TRISACRYL

Synthesis of hCG solid phase reagent The hCG-solid phase reagent was prepared by coupling hCG to TRISACRYL® GF-2000LS.

TRISACRYL is a porous, spherical, polyacrylamide solid phase matrix available from IBF Savage, Md. Prior to coupling with hCG the TRISACRYL was activated by extensive washing with water, ethanol, acetone and dimethylformamide (DMF) and then reacting the TRISACRYL with carbonyl diimidizole (CDI) in DMF. The activated TRISACRYL was then coupled to hCG by the reaction of hCG with the said material in aqueous buffer (pH 10.2). Following the coupling unreacted hCG was removed from the TRISACRYL by extensive washing with 1.0 M acetic acid and neutral pH buffers.

B) Lyophilized TRISACRYL

Ligand coupled TRISACRYL was then washed four times with two volumes of a one percent solution of bovine serum albumin (BSA) using a buchner funnel. On the last wash only one half of the BSA solution was drawn through the buchner funnel. The remaining slurry (TRISACRYL and BSA solution) that remained on the filter was then transferred to a flat bottomed glass or stainless steel tray. The gel was allowed to settle in the tray, and then excess BSA solution was carefully removed from the tray by aspiration. The remaining material in the tray (ligand bound TRISACRYL) was then frozen and lyophilized.

C) TRISACRYL-AVICEL blend

Following lyophilization, the TRISACRYL is re-equilibrated in a humidity controlled environment (65°-75° F.; 20-30% relative humidity) until the TRISACRYL moisture content is between four and nine percent. It is then sieved with a mesh screen to remove aggregated particles. The TRISACRYL is then mixed with an equal weight of AVICEL® PH101 (a microcrystalline cellulose available from FMC Corporation), that had previously been defined using a 400 mesh sieve, and blended for 15 minutes using a standard V-type blender.

D) Tableting

The TRISACRYL-AVICEL blend was then tabletted using a standard (B2) sixteen station gravity feed rotary tablet press. Twenty milligram tablets were prepared using ⅜"flat face beveled edge tooling. Compression was done at approximately 60,000 PSI. The resulting tablets were hard (10 strong Cobbs units) and disintegrated rapidly upon addition to aqueous buffer solutions.

EXAMPLE 5

Uses of the Ligand Labeled Tableted Reagent

A) Separation of soluble ligands from solutions

The tableted reagent of Example 4 was utilized to capture the excess antibody-enzyme used in the assay of Example 3 in lieu of the slurry disclosed therein.

B) Separation of soluble ligands from cells and/or particles:

The tabletted reagent can be used to separate soluble ligands from cell and/or particle suspensions.

C) TRISACRYL-AVICEL as a tablet filler-binder

In addition to functioning as an antiligand, the reagent (TRISACRYL-microcrystalline cellulose) can also serve as a filler-binder delivery system for other soluble and/or insoluble reagents. For example a lyophilized protein, such as an antibody or labeled antibody is blended with a mixture of TRISACRYL and microcrystalline cellulose and compressed into a tablet. Following reconstitution of the antibody (or labeled antibody) with solvent the filler-binders could be removed from the antibody solution by filtration and/or gravity.

EXAMPLE 6

Properties of the Tablets

A) Hardness

The tablets prepared according to Example 4 exhibited unusual hardness. The tablets measured 7-10 Strong Cobb units on the hardness scale.

B) Disintegration

Nonetheless, they disintegrated completely within two or three seconds upon placing them in an aqueous solution. The disintegrated tablets settled completely and rapidly (60 to 90 seconds) following disintegration.

C) Non Specific Binding

In addition, the tabletted reagent of this invention exhibited very low non specific binding. Non-specific binding was tested using a tabletted reagent of this invention where the TRISACRYL particles were conjugated with hCG antigen. An antibody enzyme conjugate not specific to hCG, namely, anti-digoxin galactosidase conjugate was added to a solution to which the hCG tablet was dissolved. If the components of the tablet exhibited significant non-specific binding, some detectable separation of the anti digoxin/galactosidase conjugate from solution would have been observed. However, little separation was observed. Non-specific binding is believed to be between 5-14%.

The binding of anti hCG antibody/galactosidase conjugate to TRISACRYL particles without any antigen was also tested. Little non specific binding of this conjugate was observed (i.e. between 5-14%).

EXAMPLE 7

Tableting of acetyl ouabain-BSA-TRISACRYL

Acetyl ouabain BSA-TRISACRYL was prepared according to procedures described in copending U.S. application Ser. No. 07/035,673 entitled "Diagnostic Immunoassay by Solid Phase Separation for Digoxin" which was filed Apr. 7, 1987 and is incorporated herein by reference. The acetyl ouabain BSA was then treated with 0.1% BSA, lyophilized and tabletted following the procedures described in Example 4.

EXAMPLE 8

Tableting of antibody-TRISACRYL

The coupling of antibodies to carbonyldiimidizole activated TRISACRYL is accomplished by procedure described in Example 4A. Therefore, an antibody coupled to TRISACRYL can be lyophilized and tabletted using the procedures described for the lyophilization and tableting of hCG-TRISACRYL in Example 4.

EXAMPLE 9

Tableting of BioGel

A sample of BioGel® P-6, a polyacrylamide porous particle (BioRad Laboratories, Richmond, Calif.), was washed with water, then washed with a 0.1% solution of bovine serum albumin (BSA), and then lyophilized. A portion of the lyophilized material was mixed with an equal weight of microcrystalline cellulose, and then compressed into 25 mg tablets. The tablets were hard (2-4 strong Cobb units) and dissolved readily when dropped into a water solution.

Example 10

Tableting of SEPHAROSE

A sample of DEAE-SEPHAROSE®, an agarose based ion exchange matrix (Pharmacia Corp., Piscataway, N.J.), was washed with water, then washed with a 0.1% solution of BSA, and then lyophilized. A portion of the lyophilized material was mixed with an equal weight of microcrystalline cellulose and then compressed into tablets. The tablets were hard (2-4 strong-Cobb units), and dissolved readily when dropped into water.

EXAMPLE 11

Tableting of SEPHADEX

A sample of SEPHADEX G-100, dextran based, porous gel filtration particles (Pharmacia Corp., Piscataway, N.J.), was washed with water, washed with a 0.1% BSA solution, and then lyophilized. A portion of the lyophilized material was mixed with microcrystalline cellulose to form a blend that was 90% microcrystalline cellulose and 10% SEPHADEX by weight. Portions of the blend were compressed into tablets that were hard (4.0 strong Cobb units), and dissolved readily when dropped into water.

EXAMPLE 12

TRISACRYL/Microcrystalline Cellulose Proportions

Tablets were prepared from TRISACRYL only, from microcrystalline cellulose only, and from various proportions of both TRISACRYL and microcrystalline cellulose. Tablets prepared with TRISACRYL only required excessive force (in excess of 1500 pounds) for compression, and were difficult to remove from the die because the tablets stuck to and crumbled upon ejection from the die. However, adding microcrystalline cellulose to TRISACRYL in a 75% TRISACRYL-25% microcrystalline cellulose ratio resulted in tablets that were a) readily ejected from the tablet die, b) hard (2-4 strong Cobb units) and c) disintegrated rapidly (2-3 seconds) upon the addition of $H_2O$. These experiments demonstrate that microcrystalline cellulose functions as both a lubricant and a filler-binder when it is blended and tabletted with TRISACRYL.

Tablets of microcrystalline cellulose only were approximately the same hardness as those prepared from the TRISACRYL-microcrystalline cellulose blends and were easily ejected from the dye. However, such tablets did not disintegrate quickly when placed in water, even after a minute. However, the addition of as little as 10% (by weight) of TRISACRYL to microcrystalline cellulose results in a tablet that is not only hard (2-4 strong-Cobb units) but completely disintegrates when placed in water (within five seconds). Thus, the TRISACRYL component functions as a tablet disintegrant.

EXAMPLE 13

Tableting of an anti hCG antibody to TRISACRYL

Since it has been shown that the protein molecule hCG can be covalently coupled to TRISACRYL (Example 4) it follows that an antibody to hCG (or an other antigen) can be coupled using the same coupling procedure. Briefly this involves activating the TRISACRYL with carbonyldiimidazole. The activated TRISACRYL is then washed with H20 and cold coupling buffer (pH 10.2) and then reacted with the antibody in pH 10.2 buffer. Following the coupling reaction the antibody TRISACRYL is washed extensively with water, 1.0 molar acetic acid, water and finally 0.1% BSA from which it is lyophilized. Following lyophilization, the TRISACRYL (antibody bound) is blended with an equal weight of microcrystalline cellulose and compressed into tablets.

EXAMPLE 14

Preparation of a Cocaine (analog) TRISACRYL Tablet

A tablet that contains either cocaine or a cocaine analog is prepared using procedures described within for the preparation of an hCG tablet. In place of hCG a protein conjugate with either cocaine or a cocaine analog is used.

EXAMPLE 15

Preparation of a tetrahydrocannabinol (THC) TRISACRYL Tablet

A tablet that contains either THC or analog is prepared using procedures described within for the preparation of an hCG tablet. In place of hCG a protein conjugate with either THC or one of its analogs is used.

EXAMPLE 16

Preparation of a lysergic acid (LSD) TRISACRYL Tablet

A tablet that contains either LSD, or an analog, is prepared using procedures described within for the preparation of an hCG tablet. In place of hCG, a protein conjugate with either LSD, or one of its analogs, is used.

EXAMPLE 17

Tableting of an antibody-enzyme utilizing a microcrystalline cellulose-TRISACRYL blend In addition to functioning as a ligand or anti-ligand support, the TRISACRYL can also function as a disintegrant and when blended with microcrystalline cellulose the resulting blend can be utilized as a filler-binder lubricant-disintegrant delivery system for other dry reagents. As an example a lyophilized protein, such as an antibody or labeled antibody can be blended with a mixture of TRISACRYL-microcrystalline cellulose and compressed into a tablet. More specifically, we have tableted an anti digoxin-β galactosidase (antibody-enzyme, A/E) conjugate. A portion of the A/E conjugate in dilute phosphate buffer (0.1 M phosphate, 0.1 M NaCl, 1 mM MgCl₂, 0.1% BSA) was diluted (5:1) with a mannitol solution such that the final mannitol concentration was approximately 1.8%, and the total concentration of solids was approximately 45 mg/ml in the solution. Portions of this solution were lyophilized and then blended 1:9 with a blend of TRISACRYL-microcrystalline cellulose (1:1) and tableted by direct compression. The resulting tablets were hard and disintegrated readily upon addition of water or buffer. Typically 3.0 mL of TDx buffer (available from Abbott Laboratories, North Chicago, Ill.) was added to one tablet that was contained in a small test tube. The tube was shaken a few times to disintegrate the tablet. After three minutes, the insoluble filler-binders settled to the bottom of the tube, and approximately 2.5 mL of the supernatant, which contained dissolved antibody-enzyme, was withdrawn from the tube. The ability of the antibody enzyme to specifically bind digoxin was evaluated using the procedure described in Example 2. In a typical experiment, approximately 83% of the antibody enzyme bound to a digoxin analog solid phase while 85% of the control antibody-enzyme (that had not been lyophilized or tableted) was bound. When similar experiments were performed in the presence of an inhibitor 4.0 mg/mL digoxin) the captures were approximately 36% and 28% respectively for the test and control antibody enzyme preparations. Thus, the binding characteristics of the tableted antibody enzyme were nearly identical to the untableted control.

From this disclosure, other modifications to these specific examples will be apparent to those of ordinary skill in the art. Such modifications are to be included within this invention, unless the claims which follow explicitly state otherwise.

We claim:
1. An immunoassay method for detecting an analyte in a test sample, which method comprises the steps of:
   a) forming a reaction mixture of the test sample with a molar excess of labeled antibody whereby said labeled antibody, specifically binds said analyte to form a complex with any analyte present in said test sample;
   b) contacting said reaction mixture with a tabletted reagent comprising polyacrylamide particles and microcrystalline cellulose and which dissolves in said reaction mixture to release said polyacrylamide particles and said microcrystalline cellulose at a sedimentation rate of from about 5 seconds per centimeter to about 2 minutes per centimeter, said polyacrylamide particles having immobilized thereon a compound capable of specifically binding said excess labeled antibody to form a solid phase complex;
   c) allowing said polyacrylamide particles and microcrystalline cellulose and any complexes thereof to settle by gravity whereby a solid and liquid phase is formed; and
   d) measuring the amount of complex left present in said liquid phase as an indication of the present of the analyte in the test sample.

2. The method of claim 1 wherein said solid phase material has a diameter of from about 5 to about 300 microns.

3. The method of claim 1 wherein said solid phase material comprises a polymeric bead or matrix.

4. The method of claim 1 wherein said labeled antibody is an enzyme labeled antibody.

5. The method of claim 1 wherein said compound immobilized on said solid phase and capable of specifically binding any excess labeled antibody is a corresponding antigen or chemical analogue thereof.

6. A tabletted reagent for separation antibodies or ligands from solution, said tabletted reagent comprising:
   a) from about 10 to 80 percent microcrystalline cellulose; and
   b) from 20 to 90 percent of polyacrylamide particles to which a ligand specific for said antibodies is immobilized or an anti-ligand antibody specific for said ligands is immobilized.

7. The tabletted reagent of claim 6 wherein said immobilized ligand is acetyl ouabain.

8. The tabletted reagent of claim 6 wherein said immobilized anti-ligand antibody comprises anti-hCG.

9. The method of claim 1 wherein said ligand is cocaine, its metabolites or analogs.

10. The tabletted reagent of claim 6 wherein said ligand is tetrahydrocannabinol.

11. The tabletted reagent of claim 6 wherein said separated ligand is lysergic acid (LSD).

12. The tabletted reagent of claim 6 comprising from about 60 to 40 percent of said cellulose, and from 40 to 60 percent of said polyacrylamide particles.

13. The tabletted reagent of claim 12 including 50% of said cellulose, and 50% of said polyacrylamide parties.

14. A method of separating antibodies from a solution, said method comprising the steps of:
   a) adding to said solution a tabletted reagent including from about 10 to 80 percent microcrystalline cellulose and from about 20 to 90 percent of polyacrylamide particles coated with a ligand specific to said antibodies, whereby said tabletted reagent dissolves in said solution to release said particles wherein said particles settle at a sedimentation rate of from about 5 seconds per centimeter to about 2 minutes per centimeter whereby said antibodies will bind to and settle with said particles; and
   b) decanting said solution to separate said antibodies bound to said settled particles form said solution.

15. The method is recited in claim 14 wherein said ligand comprises acetyl ouabain.

16. The method of claim 14 wherein said ligand is ouabain triacetate.

17. The method of claim 14 wherein said regent includes 50 percent microcrystalline cellulose and 50 percent polyacrylamide particles.

18. A tabletted reagent for introducing antibody-enzyme conjugate into solution, comprising:
   a) from about 10 to 80 percent microcrystalline cellulose;
   b) from about 20 to 90 percent of polyacrylamide particles; and
   c) an antibody-enzyme conjugate protein.

19. The tabletted reagent of claim 8 wherein said antibody-enzyme conjugate is anti-digoxin-β-galactosidase conjugate.

* * * * *

UNITED STATES PATENT AND TRADEMARK OFFICE
CERTIFICATE OF CORRECTION

PATENT NO. : 5,229,268
DATED : July 20, 1993
INVENTOR(S) : T.A. Pry, et al.

It is certified that error appears in the above-identified patent and that said Letters Patent is hereby corrected as shown below:

Title Page, column 1, after Appl. No.: delete "172,503" and insert --125,035--.
Column 11, line 66, delete "present" and insert --presence--.
Column 12, line 12, delete "separation" and insert --separating--.
Column 12, line 24, delete "1" and insert --6--.
Column 12, line 64, delete "8" and insert --18--.

Signed and Sealed this

Twenty-ninth Day of March, 1994

Attest:

BRUCE LEHMAN

Attesting Officer    Commissioner of Patents and Trademarks